US012440224B1

(12) United States Patent
Pedicini

(10) Patent No.: US 12,440,224 B1
(45) Date of Patent: Oct. 14, 2025

(54) ANVIL ASSEMBLY AND IMPACT ASSEMBLY FOR AN ORTHOPEDIC IMPACTOR TOOL

(71) Applicant: Fidelis Partners, LLC, Cheyenne, WY (US)

(72) Inventor: Christopher Pedicini, Brentwood, TN (US)

(73) Assignee: FIDELIS PARTNERS, LLC, Cheyenne, WY (US)

(*) Notice: Subject to any disclaimer, the term of this patent is extended or adjusted under 35 U.S.C. 154(b) by 0 days.

(21) Appl. No.: 19/073,013

(22) Filed: Mar. 7, 2025

Related U.S. Application Data

(60) Provisional application No. 63/728,398, filed on Dec. 5, 2024.

(51) Int. Cl.
*A61B 17/16* (2006.01)

(52) U.S. Cl.
CPC ...... *A61B 17/1631* (2013.01); *A61B 17/1604* (2013.01)

(58) Field of Classification Search
CPC ............ A61B 17/1604; A61B 17/1631; A61B 17/921; A61B 17/92; A61B 2017/924; A61B 2017/922; A61F 2/4607
See application file for complete search history.

(56) References Cited

U.S. PATENT DOCUMENTS

2017/0020536 A1* 1/2017 Johnson ................. A61B 17/92
2022/0226033 A1* 7/2022 Slocum ................. A61F 2/4603
2022/0323134 A1* 10/2022 Lyon ...................... A61B 17/92

OTHER PUBLICATIONS

International Search Report and Written Opinion issued Aug. 12, 2025 in corresponding International Patent Application No. PCT/US2025/035879, 6 pages.

* cited by examiner

*Primary Examiner* — Amy R Sipp
(74) *Attorney, Agent, or Firm* — XSENSUS LLP

(57) ABSTRACT

In some implementations, an adjustable anvil assembly and/or a floating impact assembly may be used in an orthopedic impactor tool to provide linear impacts. The adjustable anvil assembly may include a rotatable anvil portion and a non-rotatable anvil portion. The rotatable anvil portion may be rotatable relative to the non-rotatable anvil portion. The floating impact assembly may include a linear motion converter that interfaces with a thrown mass of the orthopedic impactor tool via a floating coupling interface.

21 Claims, 9 Drawing Sheets

ANVIL ASSEMBLY AND IMPACT ASSEMBLY FOR AN ORTHOPEDIC IMPACTOR TOOL

CROSS-REFERENCE TO RELATED APPLICATION

This application claims the benefit of U.S. Provisional Application No. 63/728,398, filed Dec. 5, 2024, which is incorporated herein by reference in its entirety.

BACKGROUND

Impactor tools are designed to deliver an impact force to a target object or material. The impactor tools are commonly used in various industries and applications where precise and controlled force is required to perform tasks, such as fastening, shaping, breaking, and/or compacting tasks.

SUMMARY

Some implementations described herein relate to orthopedic impactor tool, comprising: a linear motion converter; a thrown mass operatively coupled to the linear motion converter; and an adjustable anvil assembly including a rotatable anvil portion and a non-rotatable anvil portion, wherein the rotatable anvil portion is rotatable relative to the non-rotatable anvil portion, wherein the non-rotatable anvil portion is fixedly connected to the orthopedic impactor tool, wherein, during an operational cycle of the orthopedic impactor tool, the linear motion converter communicates the linear motion to the thrown mass along an impact axis defined by the linear motion converter, wherein the linear motion, communicated to the thrown mass, causes the thrown mass to accelerate and impact the non-rotatable anvil portion, and wherein impacting the non-rotatable anvil portion imparts a linear impact force to the non-rotatable anvil portion which is communicated to the rotatable anvil portion.

Some implementations described herein relate to an orthopedic impactor tool, comprising: a motor not on an impact axis; a linear motion converter on the impact axis and operatively coupled to the motor; a thrown mass operatively coupled to the linear motion converter on the impact axis; and an anvil, wherein, during a first time of an operational cycle of the orthopedic impactor tool, the motor drives the linear motion converter causing the linear motion converter to accelerate the thrown mass in an impact direction, wherein, at a second time during the operational cycle, a rotational speed of the linear motion converter is reduced prior to or coincident with the thrown mass impacting the anvil, imparting an impact force to the anvil, and wherein the impact force occurs on a different axis than a motor axis.

Some implementations described herein related to an orthopedic impactor tool, comprising: a motor operable along a motor axis; a linear motion converter, operatively coupled to the motor, operable along an impact axis that is independent from the motor axis; a thrown mass operatively coupled to the linear motion converter; an anvil; a sensor configured to detect data associated with a position of the thrown mass during an operational cycle of the orthopedic impactor tool; and a floating coupling interface that allows, based on the data, the linear motion converter to be decoupled from the thrown mass at a time before or coincident with when the thrown mass impacts the anvil.

Some implementations described herein related to an orthopedic impactor tool, comprising: a motor; a linear motion converter operatively coupled to the motor, wherein the linear motion converter is at least one of: a lead screw and lead nut assembly, a belt and pulley assembly, a chain and sprocket assembly, a rack and pinion assembly, or a ball screw assembly; a thrown mass operatively coupled to the linear motion converter; a bumper; and an anvil including at least one impact surface and operable according to an anvil stroke; wherein, during an operational cycle of the orthopedic impactor tool, the motor generates rotational motion that drives the linear motion converter, wherein the linear motion converter, while being driven by the rotational motion, converts the rotational motion into linear motion and communicates the linear motion to the thrown mass, wherein the linear motion, communicated to the thrown mass, causes the thrown mass to accelerate and impact the at least one impact surface imparting a linear impact force on the anvil, and wherein the anvil stroke is less than or equal to 13 millimeters before the thrown mass impacts a bumper.

DETAILED DESCRIPTION OF EXAMPLE EMBODIMENTS

Figure 1A:
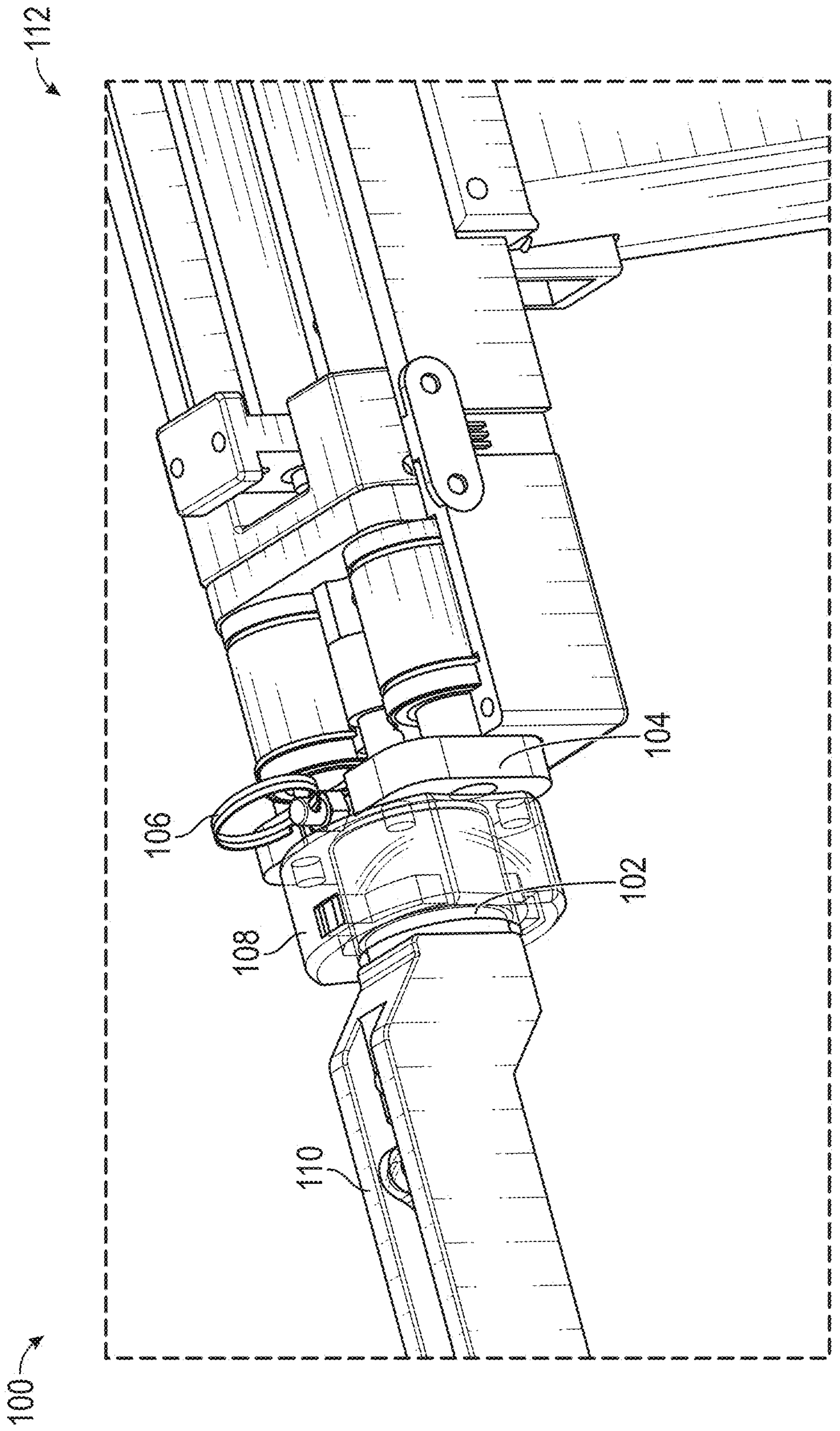
FIGS. 1A-1D are diagrams of an example adjustable anvil assembly for an orthopedic impactor tool.
Figure 1B:
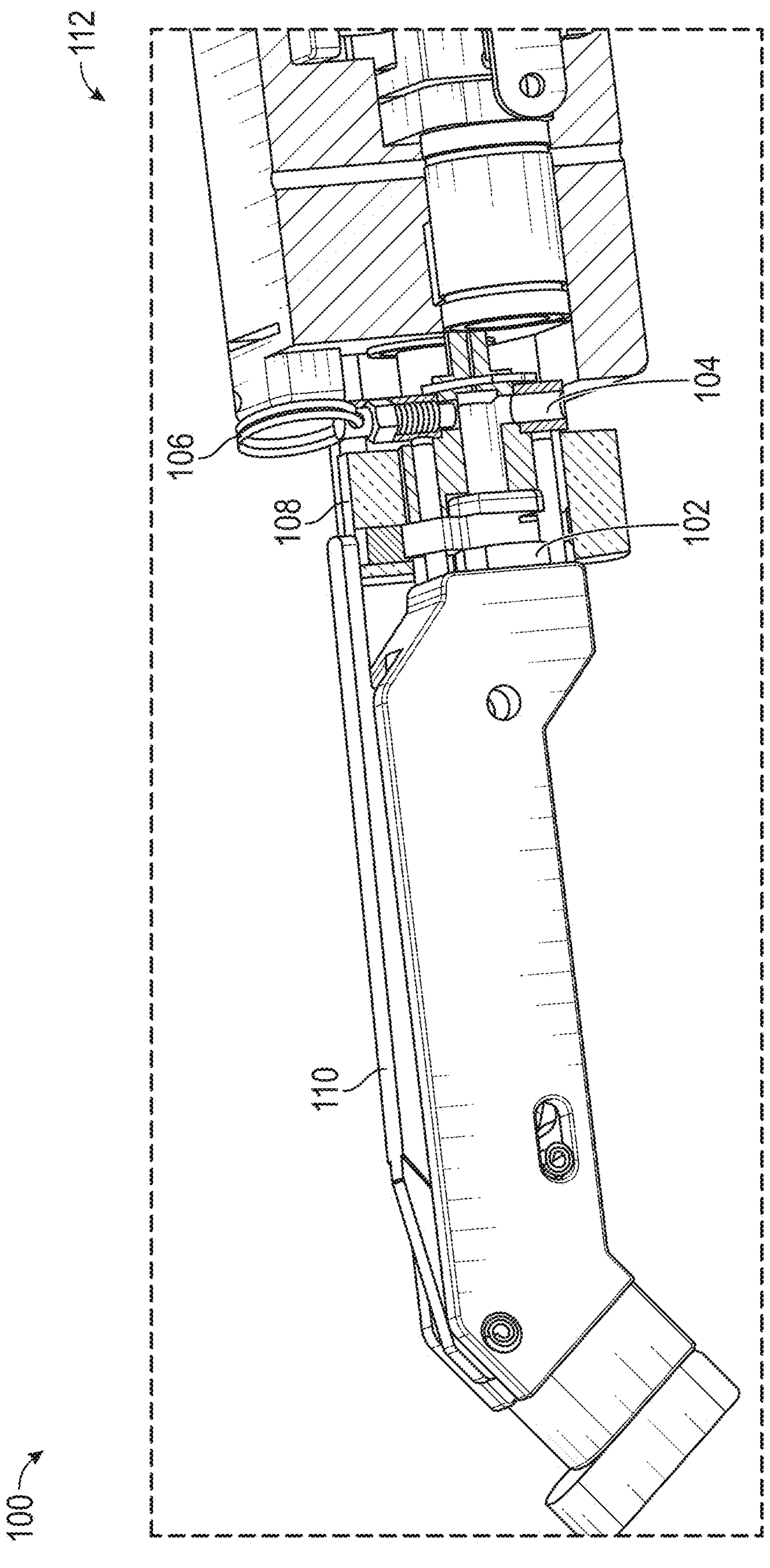

The following detailed description of example implementations refers to the accompanying drawings. The same reference numbers in different drawings may identify the same or similar elements.

Powered impactor tools are used in orthopedic procedures to drive surgical instruments, such as broaches, with controlled impacts (e.g., controlled linear impacts). However, typical powered impactor tools have several drawbacks that affect their efficiency and usability. One issue is the repositioning of the end effector, such as a broach, which often requires decoupling it from an adapter, manually rotating it, and then re-coupling it to the typical powered impactor tool. This process is time-consuming, disrupts workflow, and increases the risk of misalignment. Additionally, typical powered impactor tools struggle to effectively mitigate recoil forces generated when a thrown mass strikes an anvil. The recoil forces are transmitted through a linear motion converter to the motor, causing damage or inoperability, thus reducing the lifespan of the tool and limiting its applicability in robotic surgery. Furthermore, excessive recoil makes the typical powered impactor tools difficult for an operator to control, requiring additional effort to maintain proper positioning and stability during use. This can lead to fatigue, reduced precision, and unintended deviations in the surgical procedure.

FIGS. 1A-1D are diagrams of an example 100 associated with an anvil assembly, such as an adjustable anvil assembly that may be used with an orthopedic impactor tool that utilizes a linear motion converter (e.g., shown as an orthopedic impactor tool 112 in FIGS. 1A-1D). In some implementations, the linear motion converter may be implemented as a lead screw and lead nut assembly (e.g., including a lead screw and a lead nut), a belt and pulley assembly (e.g., including a belt and a pulley), a chain and sprocket assembly (e.g., including a chain and a sprocket), a rack and pinion assembly (e.g., including a rack and a pinion), and/or a ball screw assembly (e.g., including a ball screw and a ball nut), among other examples.

As shown in FIGS. 1A-1D, the example 100 includes a first anvil portion 102 (e.g., a selectively rotatable anvil portion), a second anvil portion 104 (e.g. a non-rotatable anvil portion), a positioning device 106, a locking device 108, and an adapter 110 (e.g., shown as a broach adapter in FIGS. 1A-1D). In some implementations, the first anvil portion 102, the second anvil portion 104, the positioning device 106, and the locking device 108 may collectively form the adjustable anvil assembly, which may be used in the orthopedic impactor tool 112, as described in more detail elsewhere herein.

Figure 1D:
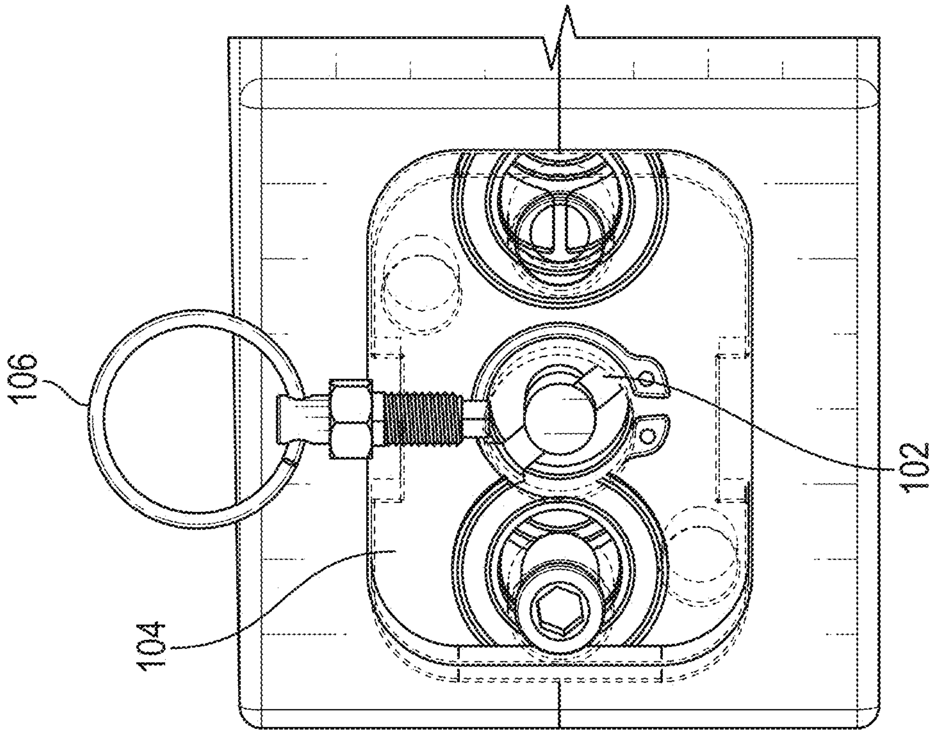
Figure 1C:
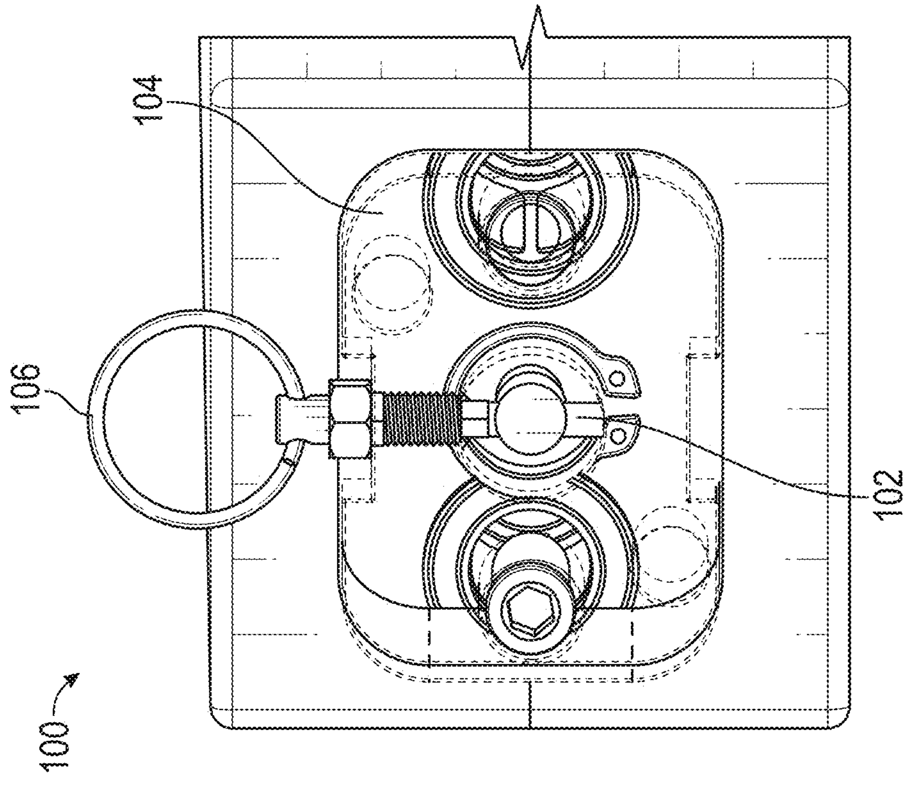

In some implementations, the first anvil portion 102 may be selectively rotatably coupled to the second anvil portion 104 via the positioning device 106, which may be operable between an engaged state (e.g., as shown in FIG. 1C) and a disengaged state (e.g., as shown in FIG. 1D). When the positioning device 106 is in the engaged state, the first anvil portion 102 may be fixedly coupled to the second anvil portion 104 in a single orientation of the multiple orientations. When the positioning device 106 is in the disengaged state, the first anvil portion 102 may be rotatable (e.g., about an impact axis, as described in more detail elsewhere herein) enabling the first anvil portion 102 to be positioned in multiple orientations (e.g., before being fixedly coupled to the second anvil portion 104 in a single selected orientation of the multiple orientations by transitioning the positioning device 106 from the disengaged state to the engaged state).

In some implementations, the positioning device 106 may allow clearance in an axial direction (e.g., along a direction of impacting) but limit rotational movement of the first anvil portion 102 about the impact axis. For example, when the positioning device 106 is in the engaged state, the positioning device 106 may restrict axial rotational movement to a range, such as a controlled range that is within approximately plus or minus 5 degrees (e.g., relative to a centered position). This locking action secures the first anvil portion 102 in a desired orientation (e.g., in the single selected orientation), ensuring precision during an orthopedic procedure.

In some implementations, the first anvil portion 102 may be positioned at an initial position relative to a fixed reference (e.g., an external reference), such as a body of the orthopedic impactor tool 112 or a fixed base (e.g., the initial position may be associated with an initial angular rotation of 0 degrees relative to a component of the orthopedic impactor tool 112). To enable movement of the first anvil portion 102 from the initial position to an adjusted position relative to the fixed reference, the positioning device 106 may be transitioned from the engaged state to the disengaged state, enabling the first anvil portion 102 to rotate into the adjusted position. After the first anvil portion 102 is rotated into the adjusted position, the positioning device 106 may be transitioned from the disengaged state to the engaged state to lock the first anvil portion 102 in place. This enables the first anvil portion 102 to be securely held in the adjusted position, providing enhanced alignment for the orthopedic procedure.

In some implementations, the adapter 110 may be releasably secured to the first anvil portion 102. For example, the first anvil portion 102 may include a receiving portion (e.g., a cavity or a recess defined by the first anvil portion 102) configured to receive a portion of the adapter 110. This allows the adapter 110 to be inserted at an insertion orientation (e.g., a defined orientation relative to the first anvil portion 102). The locking device 108 may secure the adapter 110 in the insertion orientation (e.g., the locking device 108 may be a mating engagement, a spring-loaded pin, a detent mechanism, and/or or a cam lock, among other examples, enabling a secure and stable connection between the adapter 110 and the first anvil portion 102 while allowing for quick attachment and removal as needed).

As a result, when the first anvil portion 102 rotates, the adapter 110 rotates along with the first anvil portion 102, maintaining the insertion orientation while achieving different spatial orientations corresponding to the multiple orientations of the first anvil portion 102. For example, the adapter 110 may be fixedly coupled to a broach used in an orthopedic procedure, and positioning of the broach may need to be adjusted based on a type of procedure being performed. During an anterior procedure, the broach may need to be positioned in a first spatial orientation relative to an anatomy of a patient, such as with a cutting surface aligned in a forward-facing direction. During a posterior procedure, the broach may need to be positioned in a second spatial orientation relative to the anatomy of the patient, such as with the cutting surface aligned in a rearward facing direction. In this context, an operator (e.g., a surgeon) of the orthopedic impactor tool 112 may cause the first anvil portion 102 to position the adapter 110 (and thus the broach) in a desired orientation for each procedure, rather than rotating the broach or the adapter 110 independently.

In this way, the spatial orientation of the adapter 110 is controlled by the rotation of the first anvil portion 102, not by changing the insertion direction of the adapter 110. In other words, a spatial orientation of the adapter 110 may be based on a corresponding orientation of the first anvil portion 102 rather than being based on altering a direction in which the adapter 110 is inserted into the first anvil portion 102.

As indicated above, FIGS. 1A-1D are provided as examples. Other examples may differ from what is described with regard to FIGS. 1A-1D.

FIGS. 2A-2F are diagrams of an example 200 associated with an impact assembly, such as a floating impact assembly that may be used with an orthopedic impactor tool that utilizes a linear motion converter (e.g., shown as an orthopedic impactor tool 208 in FIGS. 2A-2F). As shown in FIGS. 2A-2F, the example 200 includes a linear motion converter (e.g., shown as a lead screw 202 and a lead nut 204) and a thrown mass 206.

In some implementations, the lead screw 202, the lead nut 204, and the thrown mass 206 may collectively form a floating impact assembly, as described in more detail elsewhere herein. The orthopedic impactor tool 208 may include a linear motion converter (e.g., the lead screw 202 and the lead nut 204), the thrown mass 206, a motor 210, an anvil 212, a sensor 214, and a controller 216.

The floating impact assembly may utilize a floating coupling interface that allows the thrown mass 206 to impact the anvil 212, imparting an impact force to the anvil 212 without transmitting the impact force to the motor 210, as described in more detail elsewhere herein. For example, a rotational speed of the linear motion converter may be reduced causing the thrown mass 206 to impact the anvil 212, imparting an impact force to the anvil 212 without transmitting the impact force to the motor 210.

In some implementations, reducing the rotational speed of the linear motion converter causes at least one of the linear motion converter to decouple from the thrown mass 206 or the linear motion converter to decouple from the motor 210 at a time before or coincident with when the thrown mass 206 impacts the anvil 212. In some implementations, the floating coupling interface may allow the linear motion converter to move within a float range (e.g., one or more float ranges that are between approximately 0.05 inches and 1 inch) and the thrown mass 206 may enter a period of uncoupled motion during a time in which the linear motion converter is moving within the float range.

In some implementations, the floating coupling interface may utilize one or more spaces that enable the lead screw 202 and/or the lead nut 204 to float within the one or more float ranges. As an example, the floating coupling interface may utilize a space provided within the thrown mass 206 (e.g., shown as a space 206*a* defined within an interior of the thrown mass 206 in FIGS. 2A-2B) that enables relative movement between the lead nut 204 and the thrown mass 206 (e.g., during an operational cycle of the orthopedic impactor tool 208). In this way, the space 206*a* allows the lead nut 204 to couple to the thrown mass 206 during a first time of the operational cycle and to decouple from the thrown mass 206 during a second time of the operational cycle, as described in more detail elsewhere herein.

For example, and during the first time of the operational cycle, the motor 210 may drive the lead screw 202, which, in turn, drives the lead nut 204. This causes the lead nut 204 to couple to the thrown mass 206 and accelerate the thrown mass 206 in an impact direction (e.g., a direction toward the anvil 212 and/or an impact surface of the anvil 212). At a second time during the operational cycle, the motor 210 may refrain from driving the lead screw 202, which, in turn, causes the lead nut 204 to brake and decouple from the thrown mass 206. After the lead nut 204 decouples from the thrown mass 206, the thrown mass 206 enters a period of uncoupled motion in the impact direction before impacting the anvil 212. In this way, and in some implementations, the thrown mass 206 may impact the anvil 212, imparting an impact force to the anvil 212 without transmitting the impact force to the motor 210 and without transmitting the impact force to the lead screw 202 which may be axially coupled to one or more components of the orthopedic impactor tool 208 (e.g., a housing of the orthopedic impactor tool 208, among other examples). This reduces and/or eliminates recoil forces that may otherwise be transmitted to an operator (e.g., a surgeon, among other examples) of the orthopedic impactor tool 208, among other examples.

Decoupling the lead nut 204 from the thrown mass 206 at a time before or coincident with when the thrown mass 206 impacts the anvil 212 minimizes recoil (e.g., by isolating one or more components of the orthopedic impactor tool 208 from the thrown mass 206 during a time that the thrown mass 206 impacts the anvil 212). For example, recoil forces generated based on the impact between the thrown mass 206 and the anvil 212 are not communicated from the thrown mass 206 to the lead nut 204, the lead screw 202, nor the motor 210.

Additionally, or alternatively, the floating coupling interface may utilize a space provided within a component of the orthopedic impactor tool 208 (e.g., shown as a bushing 208*a* defining a cavity in FIG. 2C) that enables the lead screw 202 to float (e.g., during the operational cycle). In this way, the space within the bushing 208*a* allows the lead screw 202 to decouple from the motor 210 during the operational cycle.

For example, during a first time of the operational cycle, the motor 210 may drive the lead screw 202, which, in turn, drives the lead nut 204. This causes the lead screw 202 and the lead nut 204 to couple to the thrown mass 206 and accelerate the thrown mass 206 in an impact direction (e.g., in a direction toward the anvil 212 and/or an impact surface of the anvil 212). At a second time during the operational cycle, the motor 210 may refrain from driving the lead screw 202 while the thrown mass 206 continues to move, which, in turn, causes the lead screw 202 and the lead nut 204 to continue to move with the lead screw 202 floating within the space defined by the bushing 208*a* to decouple the lead screw from the motor 210 at a time before or coincident with when the thrown mass 206 impacts the anvil 212. In this way, and in some implementations, at least one of the lead screw 202 or the thrown mass 206 may define a floating coupling interface that allows the motor 210 to be decoupled from the thrown mass 206 at a time before or coincident with when the thrown mass 206 impacts the anvil 212.

In some implementations, impact energy communicated from the thrown mass 206 to the anvil 212 may be based on a rotational speed of the lead screw 202, which may be controlled by a current supplied to the motor 210. Accordingly, and in some implementations, the controller 216 may control the impact energy communicated from the thrown mass 206 to the anvil 212 by modulating the current supplied to the motor 210. For example, the controller 216 may modulate the input current (e.g., supplied to the motor 210) during a drive stroke to control the impact energy of the thrown mass 206. The sensor 214 and the controller 216 may register (e.g., detect) a position of the thrown mass 206. Based on registering the position of the thrown mass 206, the controller 216 may modulate the input current to be a percentage of the input current that is currently being supplied to the motor 210.

For example, if the input current that is currently being supplied to the motor 210 is 100% input current, the controller 216 may, based on the position of the thrown mass 206, reduce the input current being supplied to the motor 210 to 50% input current. Accordingly, rather than braking the lead screw 202 when the thrown mass 206 reaches the registered position, the input current that is supplied to the motor 210 may be reduced to 50% input current, sustaining a reduced rotational speed of the lead screw 202. This enables additional energy to be imparted to the thrown mass 206 as the thrown mass 206 travels in the impact direction, resulting in a greater overall impact energy while minimizing mechanical stresses associated with sudden braking.

In some implementations, the floating impact assembly may include (e.g., optionally) a biasing element 218 (e.g., an elastomer or spring, among other examples) which biases the lead nut 204 to a position (e.g., a position within the space 206*a*, such as a position proximate a front side of the thrown mass 206, a position proximate a rear side of the thrown mass 206, or a position centrally located within the thrown mass 206, among other examples).

Figure 2A:
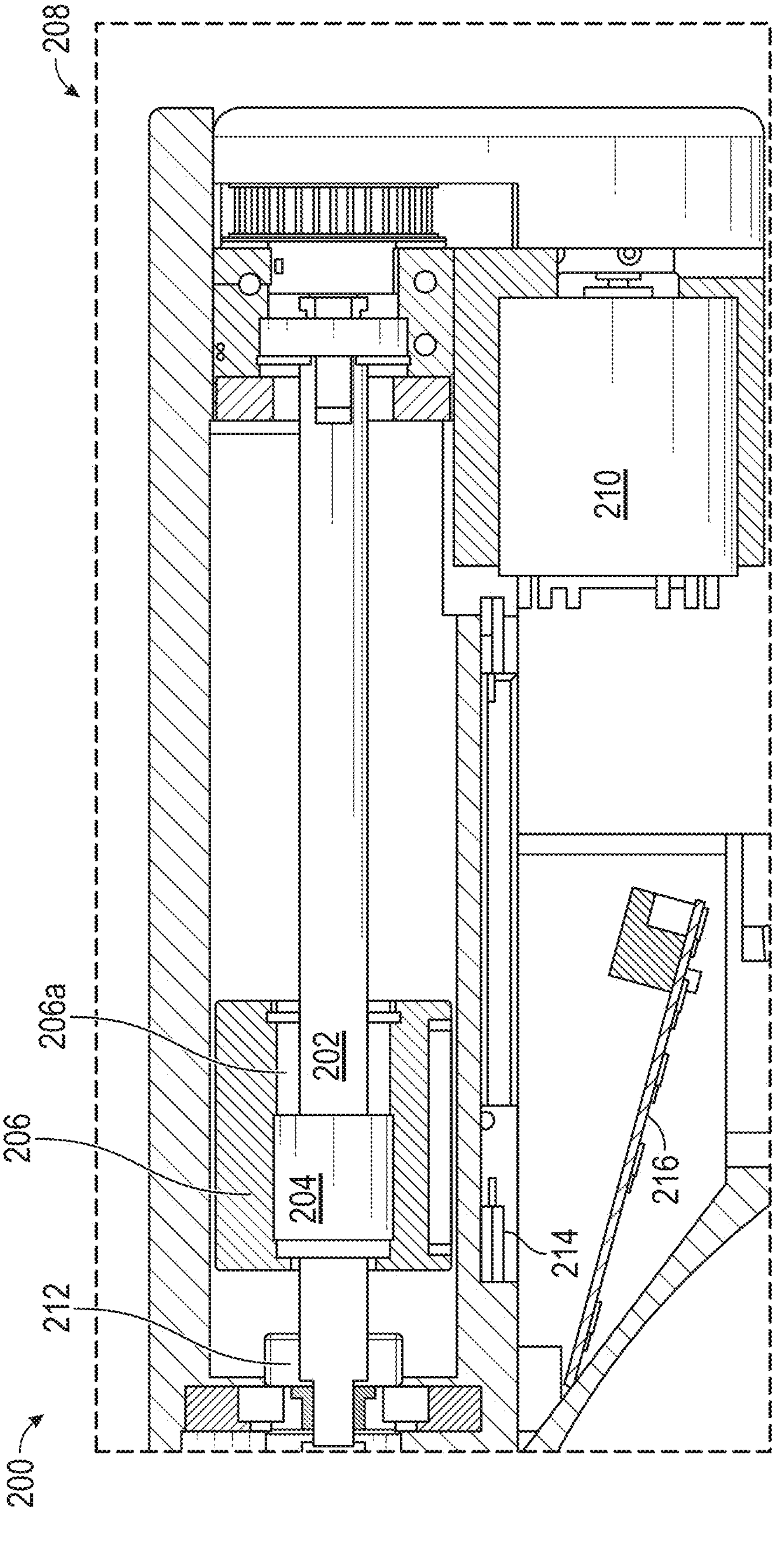
FIGS. 2A-2F are diagrams of an example floating impact assembly for an orthopedic impactor tool.
Figure 2B:
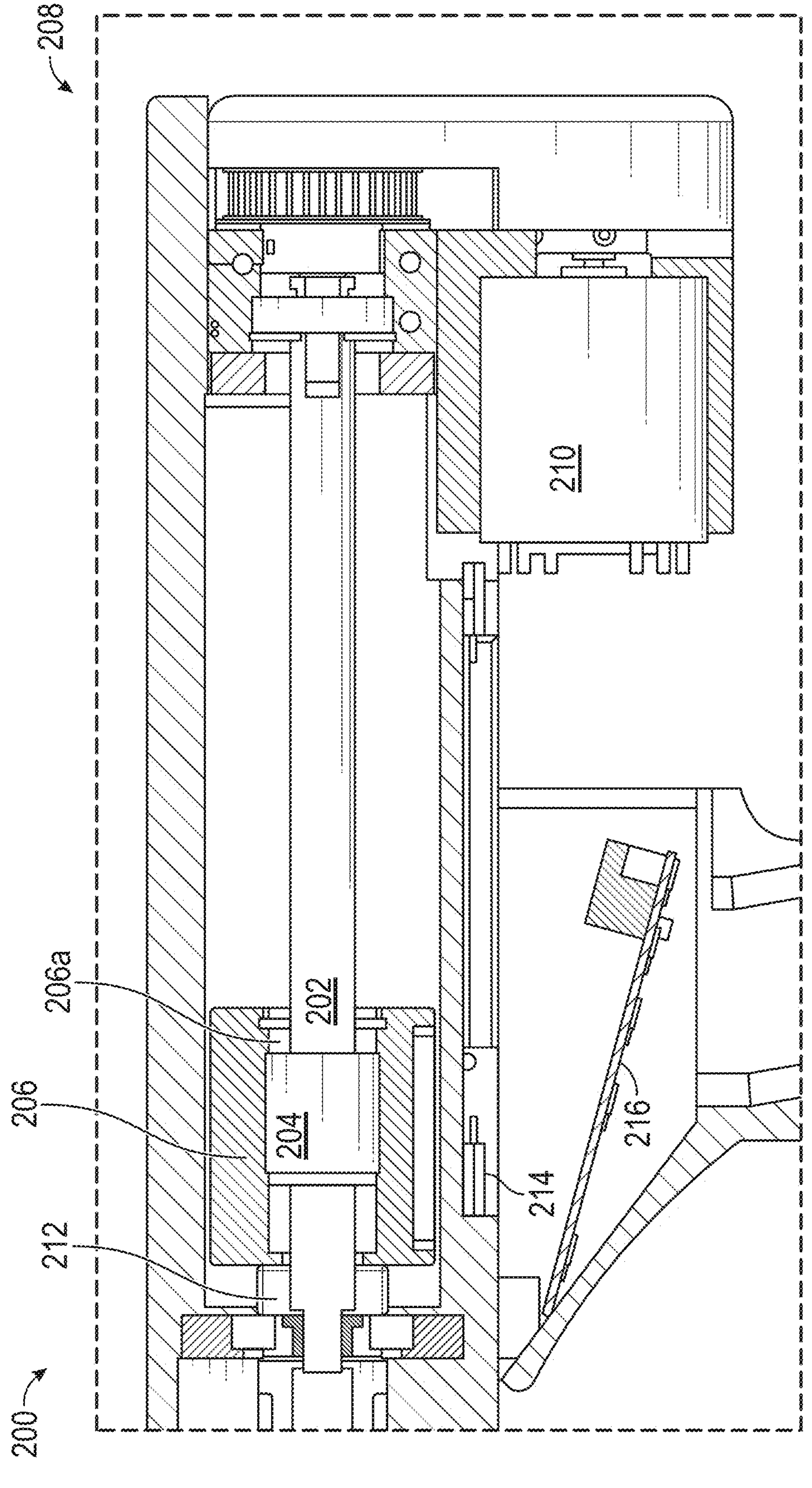
Figure 2C:
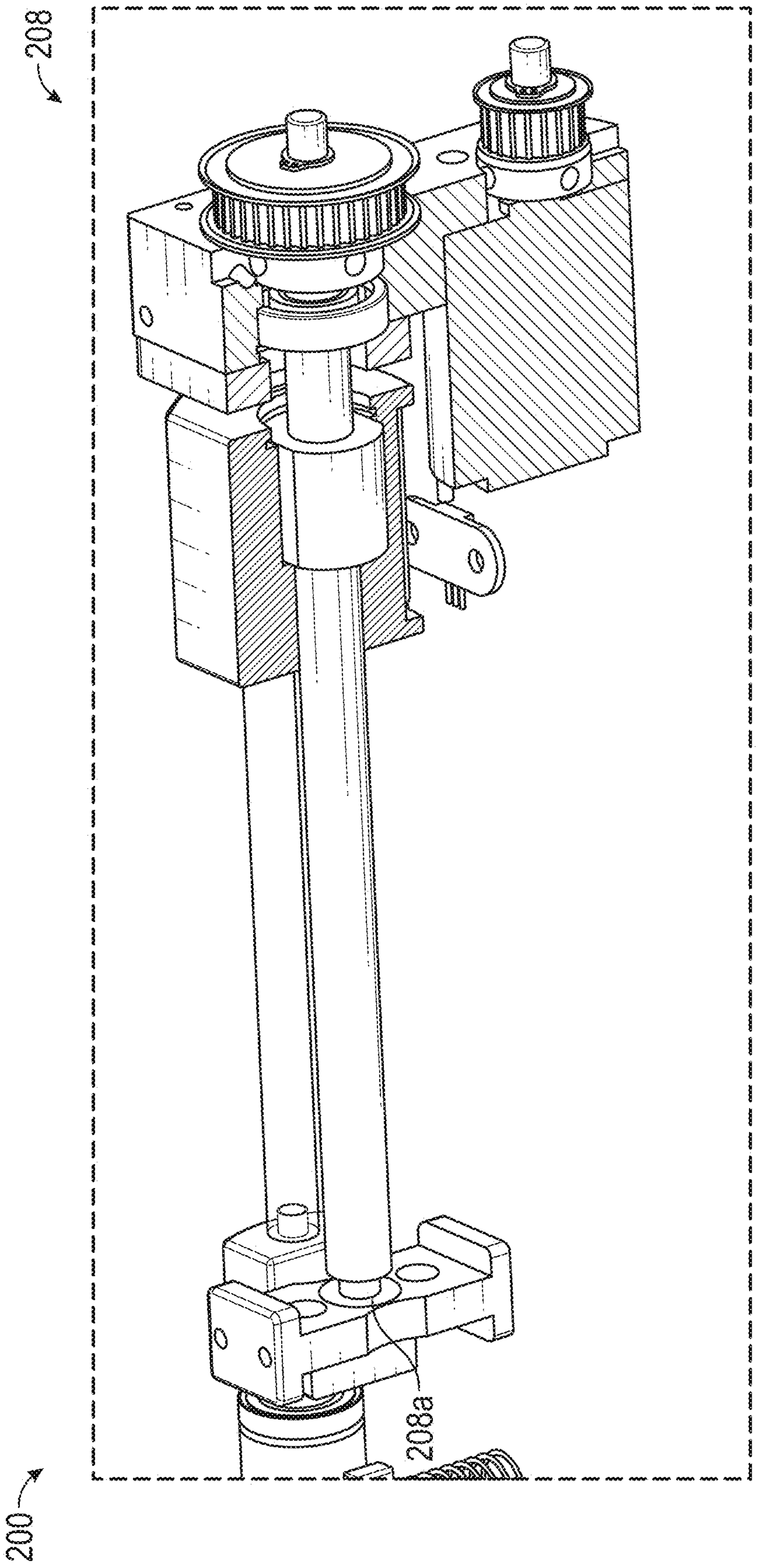
Figure 2D:
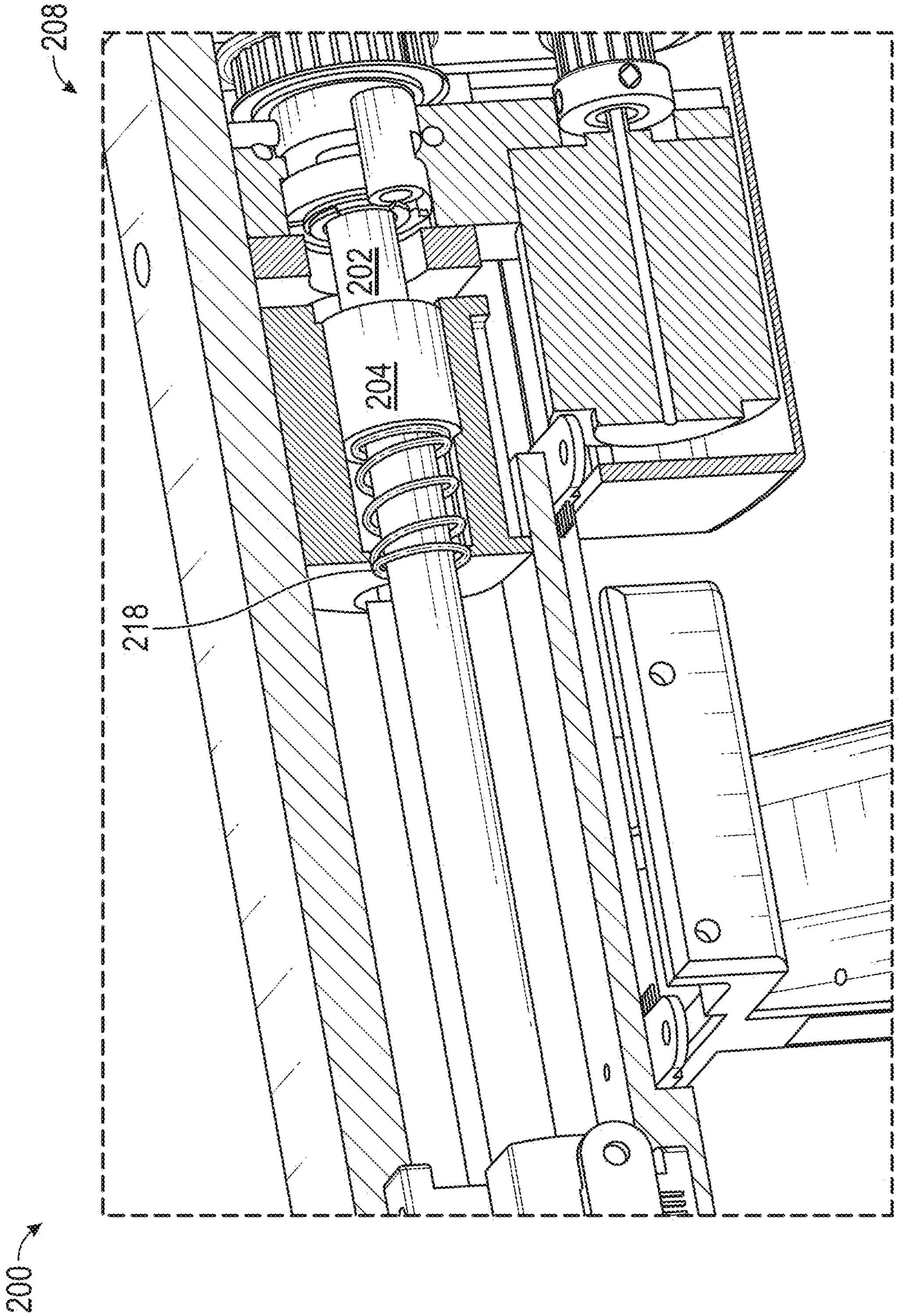

As shown in FIG. 2D, the biasing element 218 is a spring that biases the lead nut 204 in a rearward direction (e.g., proximate the rear end of the thrown mass 206). Although the biasing element 218 is shown and described as being a spring, the biasing element 218 may be any suitable biasing element, such as two springs that bias the lead nut 204 centrally within the space 206*a*. Accordingly, and in some implementations, the biasing element 218 (e.g., which is optional) improves performance of the orthopedic impactor tool 208 while still permitting the period of uncoupled motion of the thrown mass 206 in the impact direction before impacting the anvil 212 (e.g., at the ends of the drive stroke or a return stroke, among other examples).

In this way, the floating impact assembly (e.g., which enables the lead nut 204 to float within the thrown mass 206 during the operational cycle) may be used to significantly reduce recoil associated with the orthopedic impactor tool 208 relative to typical impact assemblies that do not use a floating connection interface.

Furthermore, the floating impact assembly may be used to reduce a sensitivity of electronics associated with the orthopedic impactor tool 208 (e.g., a sensitivity of the sensor 214 and/or the controller 216), providing further benefits. For example, the floating impact assembly may be used to increase a tolerance associated with timing and/or positioning errors. For example, and if the thrown mass 206 travels at a speed of 250 inches per second, a 1-millisecond error could result in a ¼-inch deviation. Accordingly, and in some implementations, at least one of the lead screw 202 and/or the lead nut 204 may be movable within a float range that is based on a velocity of the thrown mass 206 as the thrown mass 206 moves in the impact direction (e.g., a float range between approximately 0.05 inches and approximately 1 inch, among other examples). For example, and if the floating impact assembly utilizes a float range of approximately 0.25 inches, the floating impact assembly may reduce an error tolerance to 1 millisecond rather than an error tolerance of microseconds associated with typical impact assemblies that do not allow components to float. In this way, the floating impact assembly may be used to improve both the performance and cost-effectiveness of the orthopedic impactor tool 208 by enhancing error tolerance and reducing precision requirements.

In some implementations, the linear motion converter may be operable along an impact axis (e.g., shown as an impact axis X1 in FIG. 2B) and the motor 210 may be operable along a motor axis (e.g., shown as a motor axis X2 in FIG. 2B). As shown in FIG. 2B, the impact axis X1 and the motor axis X2 are non-colinear. Accordingly, and in some implementations, the impact axis X1 and the motor axis X2 may be parallel or approximately parallel to one another (e.g., extending in parallel or approximately parallel directions while remaining offset from one another).

Accordingly, and in some implementations, the orthopedic impactor tool 208 may include a motor (e.g., the motor 210) not on an impact axis (e.g., the motor may be positioned non-colinear relative to the impact axis X1) and a linear motion converter (e.g., the lead screw 202 and the lead nut 204) on the impact axis (e.g., the lead screw and the lead nut 204 may be positioned along the impact axis X1) and operatively coupled to the motor 210. In this way, impact forces (e.g., generated as a result of the thrown mass 206 accelerating and impacting the anvil 212) may occur on a different axis (e.g., the impact axis X1) than the motor axis X2. Although the impact axis X1 and the motor axis X2 are described herein as being non-colinear, the impact axis X1 and the motor axis X2 may be aligned relative to one another in any suitable manner (e.g., the impact axis X1 and the motor axis X2 may be colinear, among other examples).

Utilizing independent impact and motor axes is beneficial because reactionary shock associated with linear impacts (e.g., high energy linear impacts, among other examples) is not transmitted to the motor 210 through the linear motion converter because the motor 210 actuator is not collinearly aligned with the linear motion converter and is thus shielded from the shocks associated with the linear impacts. Isolation of the motor 210 from the shock coupled through the linear motion converter by using two separate axes unexpectedly increased a longevity of the orthopedic impactor tool 208 while also reducing the overall length of the orthopedic impactor tool 208 relative to typical powered impactor tools.

Figure 2E:
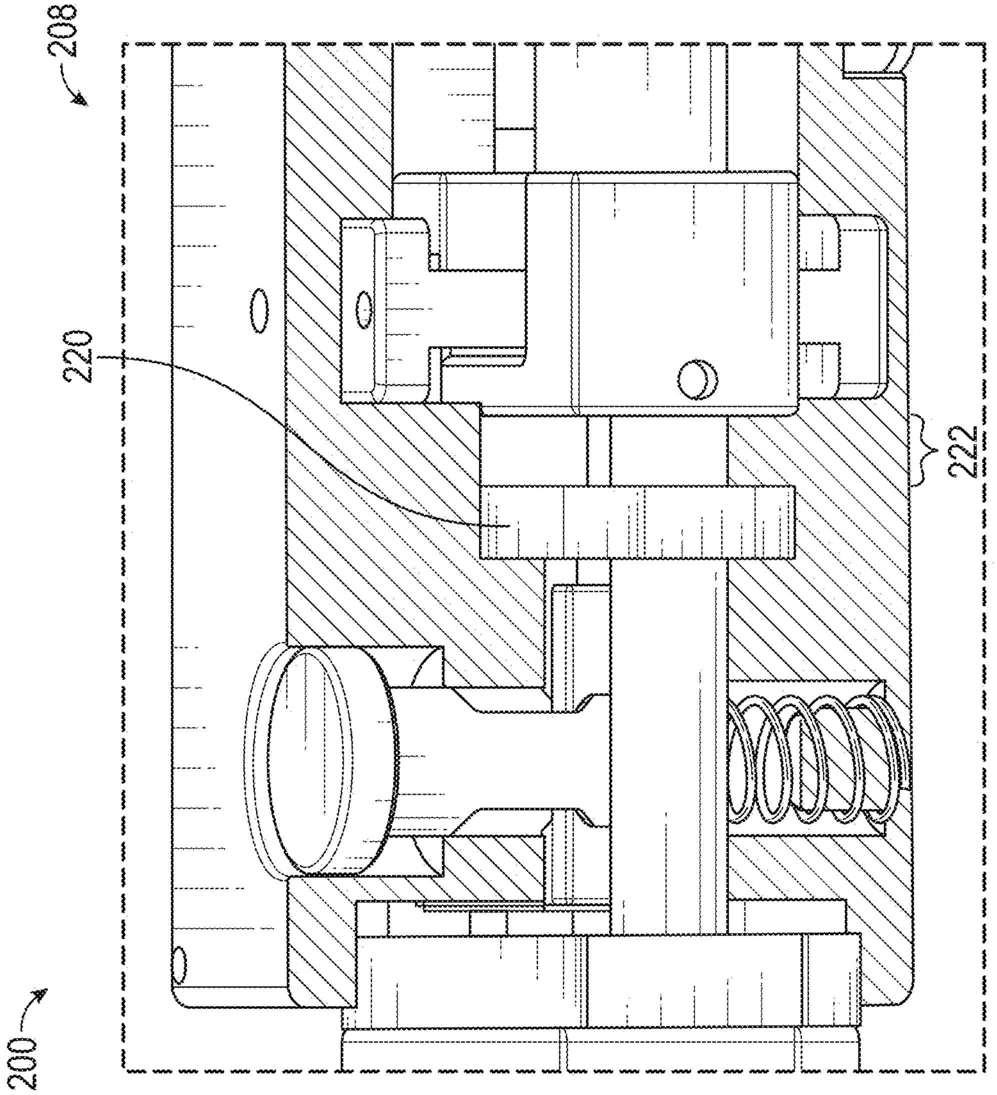

In some implementations, the orthopedic impactor tool 208 may include a bumper (e.g., shown as a bumper 220 in FIG. 2E) and the anvil 212 may be associated with an anvil stroke (e.g., shown as an anvil stroke 222 in FIG. 2E). As described herein, an "anvil stroke" may refer to a distance or an amount of movement the anvil 212 may travel before contacting the bumper 220. Accordingly, and in some implementations, the motor 210 may generate rotational motion that drives the linear motion converter (e.g., the lead screw a202 and the lead nut 204). The linear motion converter, while being driven by the rotational motion, may converts the rotational motion into linear motion and communicate the linear motion to the thrown mass 206. The linear motion, communicated to the thrown mass 206, may cause the thrown mass 206 to accelerate and impact the anvil 212 (e.g., at least one impact surface of the anvil 212) imparting a linear impact force on the anvil 212. In some implementations, the anvil stroke may be less than or equal to 13 millimeters at a time before the thrown mass 206 impacts the bumper 220 (e.g., the thrown mass 206 impacts the anvil 212 and both the thrown mass 206 and the anvil move until contacting the bumper 220).

Although the anvil stroke is described herein as being limited to less than or equal to 13 millimeters, the anvil stroke may be limited to any suitable distance, such as between 1 and 13 millimeters. It has been determined that, even with the advantage of recoil mitigation described in more detail elsewhere herein, an anvil stroke of less than 1 millimeter results in less than 50% of the kinetic energy from the thrown mass 206 being transferred to the anvil 212. It has been further discovered that an anvil stroke exceeding 13 millimeters at a time before the thrown mass 206 impacts the bumper 220 results in uncontrolled advances of a surgical implement (e.g., coupled to the orthopedic impactor tool 208) leading to inaccuracies in an associated surgical procedure and loss of control by the surgeon, such as during continuous impacting.

Figure 2F:
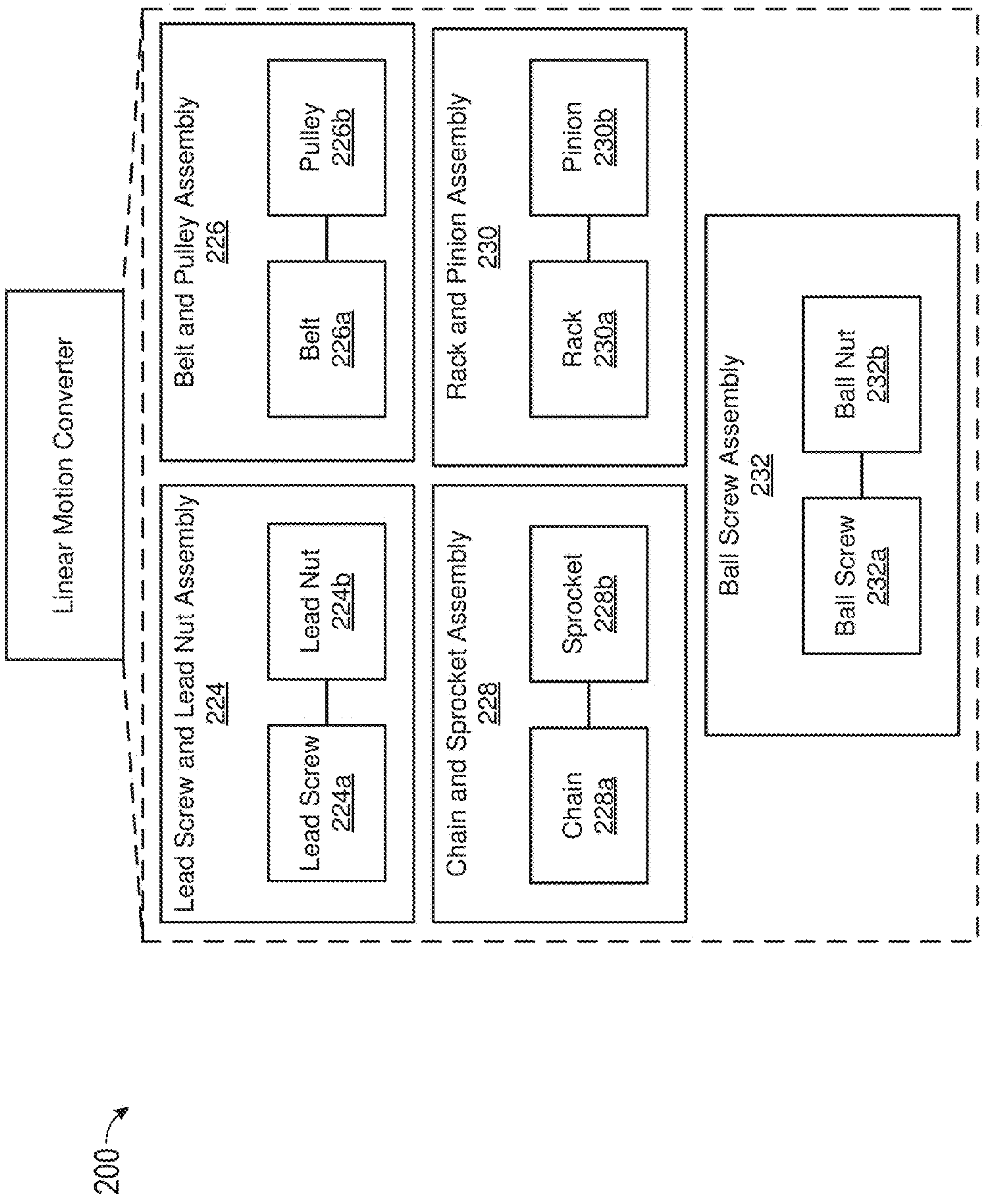

Although the linear motion converter is described herein as including the lead screw 202 and the lead nut 204, the linear motion converter may be any suitable linear motion converter, such as a lead screw and a lead nut assembly including a lead screw and a lead nut (e.g., shown as a lead screw and lead nut assembly 224 including a lead screw 224*a* and a lead nut 224*b* in FIG. 2F), a belt and pulley assembly including a belt and a pulley (e.g., shown as a belt and pulley assembly 226 including a belt 226*a* and a pulley 226*b* in FIG. 2F), a chain and sprocket assembly including a chain and a sprocket (e.g., shown as a chain and sprocket assembly 228 including a chain 228*a* and a sprocket 228*b* in FIG. 2F), a rack and pinion assembly including a rack and a pinion (e.g., shown as a rack and pinion assembly 230 including a rack 230*a* and a pinion 230*b* in FIG. 2F), and/or a ball screw assembly including a ball screw and a ball nut (e.g., shown as a ball screw assembly 232 including a ball screw 232*a* and a ball nut 232*b* in FIG. 2F), among other examples.

As indicated above, FIGS. 2A-2F are provided as examples. Other examples may differ from what is described with regard to FIGS. 2A-2F.

Although the adjustable anvil assembly is shown and described as being used with the orthopedic impactor tool 112 in connection with FIGS. 1A-1D and the floating impact assembly is shown and described as being used with the orthopedic impactor tool 208 in connection with FIGS. 2A-2F, the adjustable anvil assembly and/or the floating impact assembly may be utilized with any suitable orthopedic impactor tool (e.g., that utilizes a linear motion converter), such as an orthopedic impactor described in U.S. Nonprovisional application Ser. No. 18/889,589, filed Sep. 19, 2024 (the '589 Application), which is incorporated herein by reference in its entirety. Accordingly, the adjustable anvil assembly and/or the floating impact assembly may be utilized with any suitable components of any suitable orthopedic impactor tool, such as one or more components of the orthopedic impactor tool 112, one or more components of the orthopedic impactor tool 208, and/or one or more components described in the '589 Application.

Even though particular combinations of features are recited in the claims and/or disclosed in the specification, these combinations are not intended to limit the disclosure of various implementations. In fact, many of these features may be combined in ways not specifically recited in the claims and/or disclosed in the specification. Although each dependent claim listed below may directly depend on only one claim, the disclosure of various implementations includes each dependent claim in combination with every other claim in the claim set. As used herein, a phrase referring to "at least one of" a list of items refers to any combination of those items, including single members. As an example, "at least one of: a, b, or c" is intended to cover a, b, c, a-b, a-c, b-c, and a-b-c, as well as any combination with multiple of the same item.

In the preceding specification, various example embodiments have been described with reference to the accompanying drawings. It will, however, be evident that various modifications and changes may be made thereto, and additional embodiments may be implemented, without departing from the broader scope of the invention as set forth in the claims that follow. The specification and drawings are accordingly to be regarded in an illustrative rather than restrictive sense.

What is claimed is:

1. An orthopedic impactor tool comprising:

a linear motion converter;

a thrown mass operatively coupled to the linear motion converter; and an adjustable anvil assembly including a rotatable anvil portion and a non-rotatable anvil portion, wherein the rotatable anvil portion is rotatable relative to the non-rotatable anvil portion and includes a recess configured to receive and secure an adapter in an insertion orientation, wherein the adapter maintains the insertion orientation while the rotatable anvil portion rotates to achieve different spatial orientations, wherein the non-rotatable anvil portion is fixedly connected to the orthopedic impactor tool, wherein, during an operational cycle of the orthopedic impactor tool, the linear motion converter communicates linear motion to the thrown mass along an impact axis defined by the linear motion converter, wherein the linear motion, communicated to the thrown mass, causes the thrown mass to accelerate and impact the non-rotatable anvil portion, and wherein impacting the non-rotatable anvil portion imparts a linear impact force to the non-rotatable anvil portion which is communicated to the rotatable anvil portion.

2. The orthopedic impactor tool of claim 1, wherein the rotatable anvil portion is rotatable between multiple orientations relative to the non-rotatable anvil portion.

3. The orthopedic impactor tool of claim 1, wherein the adjustable anvil assembly further includes a positioning device, wherein the positioning device is operable between an engaged state and a disengaged state, wherein when the positioning device is in the disengaged state, the rotatable anvil portion is rotatable, and wherein when the positioning device is in the engaged state, the rotatable anvil portion is fixedly coupled to the non-rotatable anvil portion.

4. The orthopedic impactor tool of claim 1, wherein the linear motion converter operates along an impact axis, wherein the adjustable anvil assembly further includes a positioning device, wherein the positioning device is operable between an engaged state and a disengaged state, and wherein, when the positioning device is in the engaged state:

the rotatable anvil portion is secured in an orientation relative to the non-rotatable anvil portion, and the rotatable anvil portion is prevented from rotating about a rotation axis beyond a range of approximately plus or minus 5 degrees from the orientation.

5. The orthopedic impactor tool of claim 1, wherein the linear motion converter operates along an impact axis, wherein the adjustable anvil assembly further includes a positioning device, wherein the positioning device is operable between an engaged state and a disengaged state, and wherein, when the positioning device is in the engaged state:

the rotatable anvil portion is secured in an orientation relative to the non-rotatable anvil portion, and the rotatable anvil portion is permitted a clearance movement along the impact axis.

6. The orthopedic impactor tool of claim 1, further comprising:

an adapter releasably secured to the rotatable anvil portion in a fixed insertion orientation relative to the rotatable anvil portion, wherein the adapter maintains the fixed insertion orientation as the rotatable anvil portion rotates, and wherein rotation of the rotatable anvil portion causes corresponding rotation of the adapter.

7. An orthopedic impactor tool comprising:

a motor not on an impact axis;

a linear motion converter on the impact axis and operatively coupled to the motor;

a thrown mass operatively coupled to the linear motion converter on the impact axis, wherein the thrown mass includes an interior space housing at least a portion of the linear motion converter; and an anvil, wherein, during a first time of an operational cycle of the orthopedic impactor tool, the motor drives the linear motion converter causing the linear motion converter to accelerate the thrown mass in an impact direction, wherein, at a second time during the operational cycle, a rotational speed of the linear motion converter is reduced prior to or coincident with the thrown mass impacting the anvil, the thrown mass configured to impart an impact force to the anvil, wherein the linear motion converter is configured to decouple from the thrown mass based on relative movement within the interior space of the thrown mass, wherein the impact force occurs on the impact axis and the motor is on a motor axis.

8. The orthopedic impactor tool of claim 7, wherein reducing the rotational speed of the linear motion converter causes the linear motion converter to decouple from the thrown mass at a time before or coincident with when the thrown mass impacts the anvil.

9. The orthopedic impactor tool of claim 7, further comprising:

a floating coupling interface that allows the linear motion converter to move within a float range, wherein the thrown mass enters a period of uncoupled motion during a time in which the linear motion converter is moving within the float range.

10. The orthopedic impactor tool of claim 9, wherein the linear motion converter includes a lead screw operatively coupled to a lead nut, and wherein at least one of the lead screw or the lead nut is movable within the float range.

11. The orthopedic impactor tool of claim 9, wherein the float range is between 0.05 inches and 1 inch.

12. The orthopedic impactor tool of claim 7, further comprising:

a sensor, operatively coupled to the orthopedic impactor tool, that detects data indicative of a position of the thrown mass during the operational cycle; and a controller configured to cause, based on the data, an input current that is supplied to the motor to be reduced.

13. The orthopedic impactor tool of claim 7, wherein the linear motion converter comprises at least one of a lead screw and lead nut assembly, a belt and pulley assembly, a chain and sprocket assembly, a rack and pinion assembly, or a ball screw assembly.

14. The orthopedic impactor tool of claim 7, wherein, the anvil comprises a rotatable anvil portion and a non-rotatable anvil portion.

15. The orthopedic impactor tool of claim 7, wherein an anvil stroke is less than or equal to 13 millimeters.

16. An orthopedic impactor tool comprising:

a motor operable along a motor axis;

a linear motion converter operatively coupled to the motor and operable along an impact axis, a thrown mass operatively coupled to the linear motion converter, wherein the thrown mass includes an internal cavity that receives at least a portion of the linear motion converter;

an anvil;

a sensor configured to detect data associated with a position of the thrown mass during an operational cycle of the orthopedic impactor tool; and a floating coupling interface within the internal cavity that allows, based on the data, the linear motion converter to be decoupled from the thrown mass at a time before or coincident with when the thrown mass impacts the anvil.

17. The orthopedic impactor tool of claim 16, wherein the anvil comprises a rotatable anvil portion and a non-rotatable anvil portion.

18. The orthopedic impactor tool of claim 16, wherein the floating coupling interface includes one or more spaces defining a float range in which the thrown mass releases axially from the linear motion converter, and wherein the float range is between approximately 0.05 inches and 1 inch.

19. The orthopedic impactor tool of claim 16, wherein an anvil stroke is less than or equal to 13 millimeters.

20. An orthopedic impactor tool comprising:

a motor;

a linear motion converter operatively coupled to the motor, wherein the linear motion converter is at least one of:

a lead screw and lead nut assembly, a belt and pulley assembly, a chain and sprocket assembly, a rack and pinion assembly, or a ball screw assembly;

a thrown mass operatively coupled to the linear motion converter, wherein the thrown mass includes a space that accommodates relative movement between the thrown mass and the linear motion converter;

a bumper; and an anvil including at least one impact surface and operable according to an anvil stroke;

wherein, during an operational cycle of the orthopedic impactor tool, the motor generates rotational motion that drives the linear motion converter, wherein the linear motion converter, while being driven by the rotational motion, converts the rotational motion into linear motion and communicates the linear motion to the thrown mass, wherein the linear motion, communicated to the thrown mass, causes the thrown mass to accelerate and impact the at least one impact surface imparting a linear impact force on the anvil, wherein the relative movement within the space enables the thrown mass to decouple from the linear motion converter prior to impact with the anvil, minimizing recoil forces transmitted to the motor, and wherein the anvil stroke is less than or equal to 13 millimeters before the anvil impacts the bumper.

21. The orthopedic impactor tool of claim 20, wherein a motor axis and an impact axis are non-colinear.

* * * * *